United States Patent [19]

Thies et al.

[11] 4,242,341

[45] Dec. 30, 1980

[54] 2,9-DIOXATRICYCLO [4,3,1,03,7] DECANE DERIVATIVES AND PHARMACEUTICAL COMPOSITIONS

[75] Inventors: Peter W. Thies, Hanover; Akiji Asai, Wennigsen; Samuell David, Hanover, all of Fed. Rep. of Germany

[73] Assignee: Kali-Chemie Pharma GmbH, Hanover, Fed. Rep. of Germany

[21] Appl. No.: 75,706

[22] Filed: Sep. 14, 1979

Related U.S. Application Data

[62] Division of Ser. No. 904,742, May 11, 1978, which is a division of Ser. No. 770,055, Feb. 18, 1977, Pat. No. 4,163,055.

[30] Foreign Application Priority Data

Feb. 21, 1976 [DE] Fed. Rep. of Germany .... P2607106

[51] Int. Cl.$^3$ .................. A61K 31/495; A61K 31/535; C07D 405/06; C07D 413/06
[52] U.S. Cl. .......................... 424/248.55; 424/248.57; 424/250; 424/274; 544/148; 544/360; 544/368; 260/326.11 R
[58] Field of Search .................. 544/148, 360, 378; 260/326.11 R; 424/248.55, 248.57, 250, 274

[56] References Cited

U.S. PATENT DOCUMENTS 3,812,154   5/1974   Thies .................................. 424/278

*Primary Examiner*—Henry R. Jiles
*Assistant Examiner*—R. W. Ramsuer
*Attorney, Agent, or Firm*—Schwartz, Jeffery, Schwaab, Mack, Blumenthal & Koch

[57] ABSTRACT

New 2,9-dioxatricyclo[4,3,1,0$^{3,7}$] decane derivatives are disclosed which are substituted by an amino methyl group in the $C_3$ position, and which exhibit sedative, especially sleep improving properties, and which have the formula

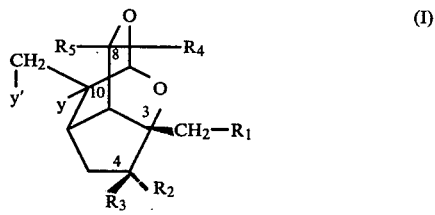

wherein
 $R_1$ represents an amino group
 one of $R_2$ and $R_3$ is hydrogen and the other represents hydroxy acyloxy or carbamyloxy or $R_2$ and $R_3$ jointly represent oxygen
 one of $R_4$ and $R_5$ is hydrogen and the other represents alkyloxy or aralkyloxy y and y' each represent hydrogen or jointly form a bond and their pharmacologically acceptable salts, as well as pharmaceutical formulations thereof.

10 Claims, No Drawings

2,9-DIOXATRICYCLO [4,3,10$^{3,7}$] DECANE DERIVATIVES AND PHARMACEUTICAL COMPOSITIONS

This is a divisional of Application Ser. No. 904,742 filed May 11, 1978, which is a divisional of Application Ser. No. 770,055 filed Feb. 18, 1977 now U.S. Pat. No. 4,163,055.

BACKGROUND OF THE INVENTION

The invention relates to new 2,9-dioxatricyclo [4,3,1,0$^{3,7}$] decane derivatives and processes for their preparation and pharmaceutical compositions thereof.

The German Offenlegungsschrifts Nos. 1,961,433, 2,027,890, 2,129,507, and 2,306,118 and the corresponding U.S. Pat. Nos. 3,812,154 and 3,917,651 disclose 2,9-dioxatricyclo[4,3,1,0$^{3,7}$] decanes which possess central nervous system depressing, narcotic neuroleptica-like and vasodilative activities.

It is a well known fact that the natural sleep comprises different phases, e.g., the classical deep sleep phase and the paradoxical sleep phase which is essential for the restitution of the organisms. None of the heretofore commercially available sleeping remedies are able to increase the paradoxical sleep phase.

SUMMARY OF THE INVENTION

It is an object of the present invention to provide new pharmacologically active 2,9-dioxatricyclo [4,3,1,0$^{3,7}$] decane derivatives which exhibit sedative properties and are low in toxicity.

It is a further object of the present invention to provide such compounds which exhibit sleep promoting and/or sleep increasing and/or sleep improving activities.

It is a further object of the present invention to provide such compounds which exhibit soporific properties without anticonvulsive side effects.

It is a special object of the present invention to provide such compounds which are effective in increasing the paradoxical sleep phase, more particularly compounds which are effective in increasing both the paradoxical, as well as the classical sleep phases.

It is a further object of the present invention to provide processes for the production of 2,9-dioxatricyclo[4,3,1,0$^{3,7}$] decane derivatives which are substituted by an amino group in the C$_3$ position, especially processes which provide for obtaining such compounds in good yields.

It is still a further object of the present invention to provide pharmaceutical solid or liquid formulations containing 2,9-dioxatricyclo[4,3,1,0$^{3,7}$] decane derivatives which are substituted by an amino group in the C$_3$ position.

It is a further object of the present invention to provide a method for the treatment or prevention of sleep disorders, especially of insomnia.

In order to accomplish the foregoing objects according to the present invention there are provided new 2,9-dioxatricyclo[4,3,1,0$^{3,7}$] decane derivatives of the formula I.

wherein
R$_1$ represents an amino group
one of R$_2$ and R$_3$ is hydrogen and the other represents hydroxy, acyloxy or carbamyloxy or R$_2$ and R$_3$ jointly represent oxygen
one of R$_4$ and R$_5$ is hydrogen and the other represents alkyloxy or aralkyloxy
y and y' each represent hydrogen or jointly form a bond and their pharmacologically acceptable salts.

Within the formula I, R$_1$ may represent an unsubstituted or a mono- or disubstituted amino radical. Suitable substituents R$_1$ are amino mono lower alkyl amino, di-lower alkylamino and especially cyclic amino radicals wherein the nitrogen preferably is a member of a heterocyclic containing 5 to 7 ring members which may contain a second heteroatom selected from the group of oxygen and monosubstituted nitrogen. Examples of such cyclic amino radicals are the piperidino, pyrrolidino, morpholino radical.

The substituent in the 4-position of the 2,9-dioxatricyclo[4,3,1,0$^{3,7}$] decane preferably is hydroxy which preferably is a β-position. The substituent in the 8-position of 2,9-dioxatricyclo[4,3,1,0$^{3,7}$] decane preferably is a lower alkyloxy group, especially methoxy. If the substituent in the 8-position is aralkyloxy, it preferably is benzyloxy.

According to the present invention, there are further provided processes for preparing the compounds of formula (I) and of intermediates which are useful for their production.

The compounds of formula (VIII)

wherein x is chlorine, bromine or iodine, R$_2$, is hydrogen or hydroxy and R$_3$, represents hydroxy or acetoxy if R$_2$, is hydrogen or hydrogen if R$_1$, is hydroxy or R$_2$, and R$_3$, jointly represent oxygen. According to a preferred embodiment of the invention, especially for preparing tertiary amines of formula I, the halomethyl compounds of formula VIII are reacted directly with an appropriate amine, preferably a secondary amine. The reaction may be performed in the presence of an aminolysis catalyst preferably in the presence of an aprotic solvent which may be the secondary amine itself. According to another embodiment the halomethyl compounds of formula VIII are first transferred into the corresponding azides, which then are reduced into primary amines, which in turn may be alkylated into secondary or tertiary amines. After introducing the amino group, the double bond in 10,11-position may be hydrogenated and/or the substituent in 4-position may be further changed in order to obtain any of the above defined substituents $R_2$ and $R_3$.

According to the present invention, there are further provided pharmaceutical compositions comprising the above described compounds of formula I or their pharmaceutically acceptable salts, and optionally an inert diluent.

Further objects, features and advantages of the present invention will become apparent from the detailed description of the invention which follows.

DETAILED DESCRIPTION OF THE INVENTION

The new compounds of formula I according to this invention and their pharmaceutically acceptable salts exhibit valuable pharmacological properties and therefore are useful in medical treatment. In particular, they are useful as sedatives since they exhibit sedative activities in animals as is indicated in standard tests, e.g., they inhibit the motility in mice upon oral administration of from 1 to 100 mg/kg body weight.

The compounds of formula I according to this invention and their pharmaceutically acceptable salts are especially useful as soporific agents in the treatment of sleep disorders since they exhibit sleep increasing and sleep improving activities in animals as is indicated in standard tests. For example, they effect a significant increase of the duration of hexabarbital induced sleep in mice upon oral administration of from 1 to 100 mg/kg body weight. Electroencephalographical tests in rats show an increase of the classical and the paradoxical sleep phases upon oral administration of from 1 to 100 mg/kg body weight.

For the above mentioned uses the administered doses can vary considerably depending on the type of the compound, the animal, the mode of administration, the treated conditions and the therapy which is desired. Usually satisfactory results are obtained with dosages between 0.075 and 100 mg/kg body weight. These doses can be administered internally, preferably orally, or parenterally. For example, daily oral doses for larger mammals can be chosen between 5 and 50 mg.

The advantageous effects of the compounds according to the present invention on the classical and the paradoxical sleep phases which have been shown in rats by electroencephalography, combined with the other sedative properties of the compounds and their low toxicity fulfill the requirements which are postulated by the latest sleep research.

The surprising activity of the new compounds will be further explained using the piperidine derivative of formula II as an example.

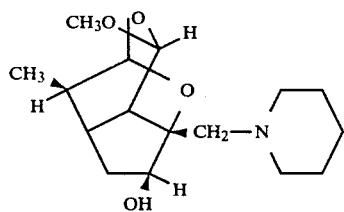

(II)

The hydrochloride of (II), test substance number 1973, and the hydrogentartarate of (II), test substance number 2961, have been used for pharmacological testing. During the screening in white mice, upon administration of oral dosages starting at 10 mg/kg the compounds effect a remarkable increase of the duration of hexobarbital induced sleep, the degree of which depends upon the administered dose, but do not exhibit any anticonvulsive activity as the soporifics of the barbiturate or benzodiazepine type do.

The compounds also exhibit a motility inhibiting activity in mice. For this activity the $ED_{50}$ is 3 mg/kg p.o.

This sedative activity has been confirmed in rats as well.

Upon observation of the sleep phases using the electroencephalography, the novel effect of the new compounds are seen: a strong increase of the paradoxical and the classical sleep phases and at the same time only a little decrease of the wake phase are observed upon oral administration of 2.5 to 80 mg/kg body weight rat. These effects are found during a 4 hour observing period, as well as during an 8 hour observing period.

The toxicity of the hydrochloride of (II) in mice is as follows: $LD_{50}$ 1136 mg/kg p.o. and 406 mg/kg i.p.

The 10,11-dehydroderivative (IIa) the pyrrolidine derivatives (III) and (IV), as well as the morpholine derivative (V) exhibit analogous properties.

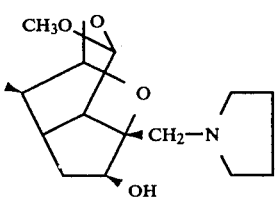

(III) (1971)

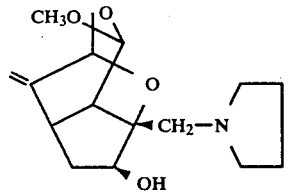

(IV) (2005)

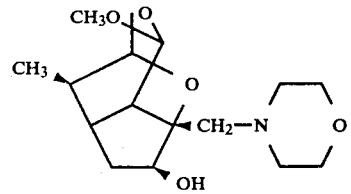

(V) (1972)

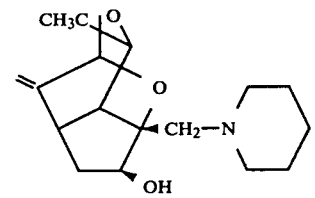

(IIa) (2973)

The secondary amine (VII), as well as the compounds which are included in the hereinbelow Tables (I–VI) exhibit corresponding activities.

(VII)

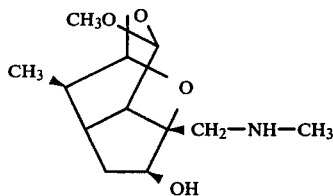

According to a further feature of the invention, there are provided pharmaceutical compositions containing at least one of the compounds of formula I or their pharmaceutically acceptable salts. The compositions may take the form of solid or liquid formulations for enteral, preferably oral, or for parenteral administration. Thus, the formulations may be in the form of capsules, tableets, coated tablets, suppositories, emulsions or solutions. These formulations may comprise conventional pharmaceutical carriers, e.g., solids, such as starch, lactose, mannit, polyvinyl pyrrolidone or liquids such as sterile water, pharmaceutically acceptable alcohols or fatty oils, and may further comprise pharmaceutical adjuvants, e.g., binders or lubricants for tabletting, stabilizing, flavoring or emulsifying agents.

According to the present invention, there are further provided processes for preparing the compounds of formula I.

Tertiary amines of formula Ig

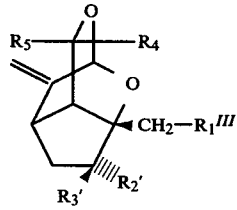
(Iq)

wherein $R_1^{III}$ represents a tertiary amino group $R_2'$ hydrogen or hydroxy and $R_3'$ represents hydroxy or acetoxy if $R_2'$ is hydrogen or hydrogen if $R_2'$ is hydroxy or $R_2'$ and $R_3'$ jointly represent oxygen and $R_4$ and $R_5$ are as defined in formula I are prepared by reacting a compound of formula VIII

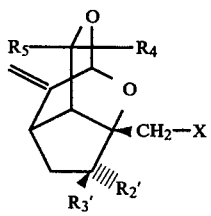
(VIII)

wherein X is chlorine bromine or preferably iodine and $R_2'$, $R_3'$, $R_4$ and $R_5$ are as defined in formula Ig with a secondary amine $R_1^{III}$.

The reaction is preferably performed in the presence of a basic compound such as sodium or potassium hydrogen carbonate. A solvent preferably an aprotic liquid, e.g., dimethyl formamide dimethyl sulfoxide or hexamethyl phosphoric acid triamide may be added. The reaction temperature preferably is between about zero and about 200° C., especially about 25° to 180° C.

Depending on the reaction conditions an acetoxy group $R_2'$ or $R_3'$ may be at least partially hydrolyzed during the reaction.

The secondary amino compounds of formula In

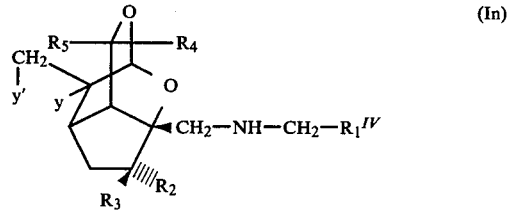
(In)

wherein $R_2$, $R_3$, $R_4$, $R_5$, y and y' are as defined in formula I and $R_1^{IV}$ represents alkyl or aralkyl which can be prepared by reacting a compound of formula Ih with an active derivative of an acid $R_1^{IV}$—COOH, which is selected from the group of acid halides and acid anhydrides and subsequently reducing the resulting amides.

Secondary and tertiary alkyl amino compounds of formula Io

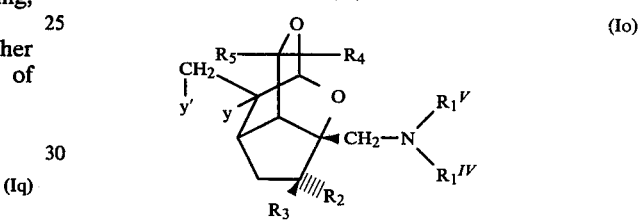
(Io)

wherein $R_2$, $R_3$, $R_4$, $R_5$, y and y' are as defined in formula I, $R_1^V$ is hydrogen or alkyl and $R_1^{VI}$ represents alkyl can be prepared by alkylating a compound of formula Ih by reacting it with an aldehyde $R_1^V$=O under reducing conditions according to known methods. Depending on the amount of aldehyde which is used, secondary or tertiary amines are obtainable. Thus, the dimethylamino derivatives of formula I are obtained by methylating compounds of formula Ih with formaldehyde under reducing conditions. Secondary amines can also be prepared from corresponding tertiary amines wherein one of the substituents is a benzyl group. Thus a compound of formula In can be prepared by debenzylating a compound of formula Im

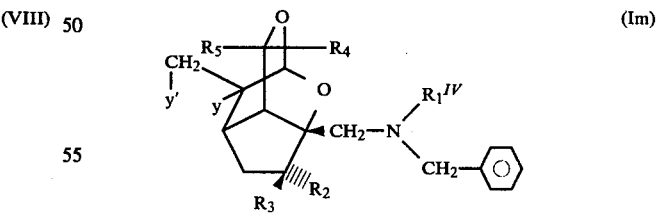
(Im)

wherein $R_1^{IV}$, $R_2$, $R_3$, $R_4$, $R_5$, y and y' are as defined in formula In.

The debenzylation is performed in a conventional manner by hydrogenolysis using a palladium catalyst.

Subsequent to the introduction of amino groups into the compounds of formula VIII, the double bond in 10,11-position may be hydrogenated and/or the substituent in the 4-position may be further changed in order to obtain any of the above defined substituents $R_2$ and $R_3$. For example, compounds of formula Ik

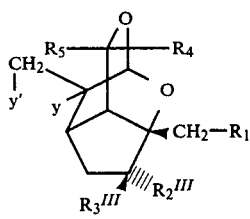

(Ik)

wherein $R_1$, $R_4$, $R_5$, y and y' are as defined in formula I, and one of $R_2^{III}$ and $R_3^{III}$ is hydrogen and the other represents acyloxy or carbamyloxy can be prepared by esterifying a compound of formula II

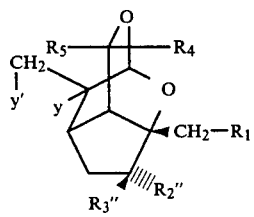

(II)

wherein $R_1$, $R_4$, $R_5$, y and y' are as defined in formula I, and one of $R_2''$ and $R_3''$ is hydrogen and the other is hydroxyl.

The esters are prepared by conventional methods, e.g., reacting the alcohols of formula (II) with appropriate acid halides or isocyanates, respectively. If the substituent $R_1$ comprises a hydroxy group, this group is also esterified during the reaction.

The 10-methyl compounds of formula Ii

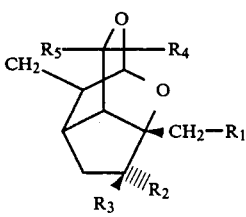

(Ii)

wherein $R_1$, $R_2$, $R_3$, $R_4$ and $R_5$ are as defined in formula I, are prepared by hydrogenating a compound of formula Ij

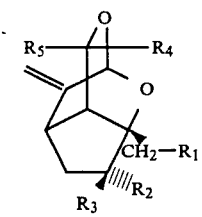

(Ij)

wherein $R_1$, $R_2$, $R_3$, $R_4$ and $R_5$ are as defined in formfula I. The hydrogenation is performed in a strongly alkaline modium in the presence of Raney nickel according to known methods.

The compounds of formula I can be recovered in free form or in form of a salt. A salt form can easily be transferred into the free form and vice versa in conventional manners. Acid addition salts of compounds of formula I can be formed with mineral acids such as hydrochloric, hydrobromic, or sulfuric acid or with organic acids such as maleinic or tartaric acid.

The compounds of formula VIII may be prepared according to the general reaction sequence which is shown below

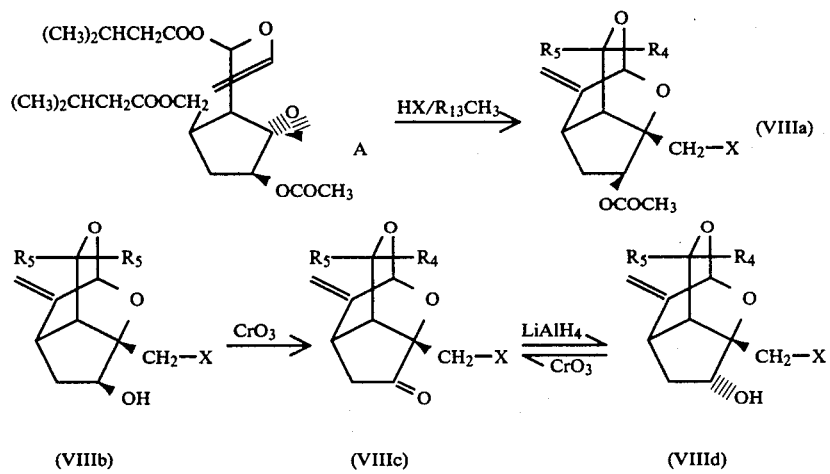

(VIIIa)

(VIIIb)     (VIIIc)     (VIIId)

As is demonstrated in the above reaction sequence in a first step dihydrovaltratum of formula A, or an extract containing dihydrovaltratum is reacted with a hydrogen halide HX in an alcohol $R_{13}OH$, wherein $R_{13}$ is alkyl or aralkyl, whereby a mixture of two isomeric compounds of formula VIIIa is formed wherein either $R_4$ or $R_5$ represents the alkyloxy or aralkyloxy group which corresponds to the alcohol $R_{13}OH$. This isomeric mixture is separated in a conventional manner.

The compounds of formula (VIIIa) may be hydrolyzed in a conventional manner to form a compound of formula (VIIIb). The 4-β-hydroxy compound of formula (VIIIb) may be oxidized into the 4-keto compound of formula (VIIIc) which in turn may be reduced with a metal hydride, e.g., Li(AlH₁) to give the 4-α-hydroxy compound of formula (VIIId). The preparation of the compounds of formula (VIIIa) may, e.g., be performed as is described in the German Offenlegungsschrift No. 2,129,507, the disclosure of which is hereby incorporated by reference. The transformation of the 4-β-hydroxy compound into the 4-α-hydroxy compound by way of the intermediate 4-keto compound may be performed according to the methods as described in German Offenlegungsschrifts No. 2,027,890 and No. 2,306,118, the disclosure of which is hereby incorporated by reference. This transformation can be effected either on the 3-halomethyl compounds of formula (VIIIb) or the corresponding final 3-aminomethyl compounds.

The invention will now be further described by the following examples.

EXAMPLE 1

Preparation of 3-piperidinomethyl-4β-hydroxy-8-methoxy-10-methylene-2,9-dioxatricyclo[4,3,1,0$^{3,7}$] decane (IIa) from 3-iodomethyl-4β-acetoxy-8-methoxy-10-methylene-2,9-dioxatricyclo[4,3,1,0$^{3,7}$] decane (VIII).

500 ml of piperidine is added to 250 g of sodium hydrogen carbonate and 190 g of (VIII). The mixture is heated to 150° in an oil bath during 4 hours under thorough stirring and reflux condenser cooling and then is cooled to room temperature. After adding 7.5 liter of ether, 1 liter of water is added for dissolving the mixture, then 200 ml of a 40% sodium hydroxide solution is added and the mixture is shaken. After separation of the etherical phase the aqueous phase is extracted 3 times more with 500 ml of ether each. The united ether extracts are dried over sodium sulfate and clarified with active carbon and filtered by suction over theorite, which is then washed with ether. The filtrate is then evaporated in a rotation evaporator first at 50° C. under reduced pressure which is produced by means of a water jet pump and subsequently at 100° C. under vacuum which is produced by means of an oil pump. Thereby 180 g of oily (IIa) are obtained. These are used without further purifying for the preparation of (II).

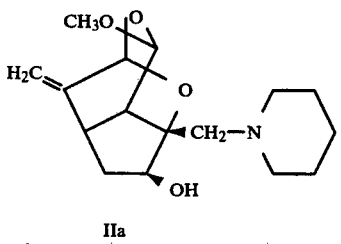

Empirical formula: C$_{16}$H$_{25}$NO$_4$
Molecular weight: 295.38
[α]$_D^{22}$ = +41.6° in methanol Empirical formula: C$_{16}$H$_{25}$NO$_4$
Molecular weight: 295.38
[α]$_D^{22}$ = +41.6° in methanol Analogous to Example 1, the following compounds are prepared (see also Table I):

3-morpholinomethyl-4β-hydroxy-8-methoxy-10-methylene-2,9-dioxatricyclo[4,3,1,0$^{3,7}$] decane (XIII), 3-(4-methyl-1-piperazinylmethyl)-4β-hydroxy-8-methoxy-10-methylene-2,9-dioxatricyclo[4,3,1,0$^{3,7}$] decane (XIV), 3-pyrrolidinomethyl-4β-hydroxy-8-methoxy-10-methylene-2,9-dioxatricyclo[4,3,1,0$^{3,7}$] decane (IV), 3-pyrrolidinomethyl-4β-hydroxy-8α-methoxy-10-methylene-2,9-dioxatricyclo[4,3,1,0$^{3,7}$] decane (XV), 3-(4-phenyl-1-piperazinylmethyl)-4β-hydroxy-8-methoxy-10-methylene-2,9-dioxatricyclo[4,3,1,0$^{3,7}$] decane (XVI), 3-(4-hydroxyethyl-1-piperazinylmethyl)-4β-hydroxy-8-methoxy-10-methylene-2,9-dioxatricyclo[4,3,1,0$^{3,7}$] decane (XVII), 3-(N,N',N'-triethylethylenediaminomethyl)-4β-hydroxy-8-methoxy-10-methylene-2,9-dioxatricyclo[4,3,1,0$^{3,7}$] decane (XVIII), 3(N-benzyl, N-methylaminomethyl)-4β-hydroxy-8-methoxy-10-methylene-2,9-dioxatricyclo[4,3,1,0$^{3,7}$] decane (XIX), 3-(N,N-dibenzylaminomethyl)-4β-hydroxy-8-methoxy-10-methylene-2,9-dioxatricyclo[4,3,1,0$^{3,7}$] decane (XX), 3-hexamethyleneiminomethyl-4β-hydroxy-8-methoxy-10-methylene-2,9-dioxatricyclo[4,3,1,0$^{3,7}$] decane (XXI), 3-(1-indolinomethyl)-4β-hydroxy-8-methoxy-10-methylene-2,9-dioxatricyclo[4,3,1,0$^{3,7}$] decane (XXII), 3-piperidinomethyl-4-oxo-8-methoxy-10-methylene-2,9-dioxatricyclo[4,3,1,0$^{3,7}$] decane (XXIII), 3-(N,N-dibutylaminomethyl)-4β-hydroxy-8-methoxy-10-methylene-2,9-dioxatricyclo[4,3,1,0$^{3,7}$] decane (XXIV), 3,4-]4-(2-pyridyl)-1-piperazinylmethyl]-4β-hydroxy-8-methoxy-10-methylene-2,9-dioxatricyclo[4,3,1,0$^{3,7}$] decane (XXV).

TABLE I

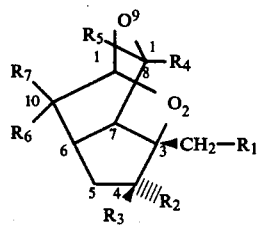

| Current Number | R$_1$ | R$_2$ | R$_3$ | R$_2$+R$_3$ | R$_4$ | R$_5$ | R$_6$+R$_7$ | Empirical Formula | Molecular Weight | mp °C. | [α]$_D^{22}$ |
|---|---|---|---|---|---|---|---|---|---|---|---|
| XIII | —N⟨  ⟩O | H | OH | — | H | OCH$_3$ | CH$_2$ | C$_{15}$H$_{23}$NO$_5$ | 297.35 | <0 | +42 |
| XIV | —N⟨  ⟩N—CH$_3$ | H | OH | — | H | OCH$_3$ | CH$_2$ | C$_{16}$H$_{26}$N$_2$O$_4$ | 310.40 | <0 | +22 |

TABLE I-continued

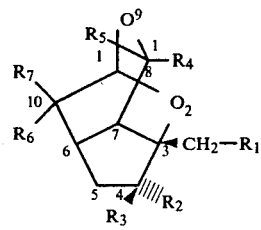

| Current Number | R1 | R2 | R3 | R2+R3 | R4 | R5 | R6+R7 | Empirical Formula | Molecular Weight | mp °C. | $[\alpha]_D^{22}$ |
|---|---|---|---|---|---|---|---|---|---|---|---|
| IV | −N⟨piperidine-like⟩ (pyrrolidine) | H | OH | — | H | OCH$_3$ | CH$_2$ | C$_{15}$H$_{23}$NO$_4$ | 281.36 | 76–77 | +36 |
| XV | −N⟨pyrrolidine⟩ | H | OH | — | OCH$_3$ | H | CH$_2$ | C$_{15}$H$_{23}$NO$_4$ | 281.36 | <0 | +122 |
| XVI | −N⟨piperazine⟩−N−C$_6$H$_5$ | H | OH | — | H | OCH$_3$ | CH$_2$ | C$_{21}$H$_{28}$N$_2$O$_4$ | 372.46 | <0 | 0 |
| XVII | −N⟨piperazine⟩N−CH$_2$−CH$_2$−OH | H | OH | — | H | OCH$_3$ | CH$_2$ | C$_{17}$H$_{28}$N$_2$O$_5$ | 340.42 | <0 | +30 |
| XVIII | −N−CH$_2$−CH$_2$−N(C$_2$H$_5$)$_2$ | H | OH | — | H | OCH$_3$ | CH$_2$ | C$_{20}$H$_{34}$N$_2$O$_4$ | 366.50 | <0 | +30 |
| XIX | −N(CH$_3$)−CH$_2$−C$_6$H$_5$ | H | OH | — | H | OCH$_3$ | CH$_2$ | C$_{19}$H$_{25}$NO$_4$ | 331.41 | <0 | +20 |
| XX | −N(CH$_2$−C$_6$H$_5$)$_2$ | H | OH | — | H | OCH$_3$ | CH$_2$ | C$_{25}$H$_{29}$NO$_4$ | 407.51 | <0 | +25 |
| XXI | −N⟨piperidine⟩ | H | OH | — | H | OCH$_3$ | CH$_2$ | C$_{17}$H$_{27}$NO$_4$ | 309.41 | <0 | +30 |
| XXII | −N⟨indoline⟩ | H | OH | — | H | OCH$_3$ | CH$_2$ | C$_{19}$H$_{23}$NO$_4$ | 328.40 | <0 | +32 |
| XXIII | −N⟨piperidine⟩ | — | — | O | H | OCH$_3$ | CH$_2$ | C$_{16}$H$_{23}$NO$_4$ | 293.35 | 68–74 | |
| XXIV | −N(C$_4$H$_9$)$_2$ | H | OH | — | H | OCH$_3$ | CH$_2$ | C$_{18}$H$_{33}$NO$_4$ | 339.48 | <0 | |
| XXV | −N⟨piperazine⟩N−(2-pyridyl) | H | OH | — | H | OCH$_3$ | CH$_2$ | C$_{20}$H$_{27}$N$_3$O$_4$ | 373.45 | 130–132 | 0 |

EXAMPLE 2

Alternative preparation of 3-morpholinomethyl-4β-hydroxy-8-methoxy-10-methylene-2,9-dioxatricyclo[4,3,1,0³,⁷] decane (XIII) from (VIII).

100 ml of morpholine are added to 38 g of (VIII) and 50 g of sodium iodide. The mixture is refluxed for 3 hours and then cooled to room temperature. After evaporating of the solvent, 200 ml of 2 N hydrochloric acid and then some methanol for dissolving the mixture are added. In order to remove acidic and neutral impurities, the solution is extracted twice with 100 ml of ether each. These etherical phases are rejected. Then 200 ml of a 2 N sodium hydroxide solution are added to the aqueous phase and the solution is saturated with sodium chloride and is extracted 5 times with 100 ml of ether each. This basic ether extract is dried over sodium sulfate, clarified with active carbon and filtered by suction over theorite. After evaporating the filtrate under vacuum, 17.92 g of an oily product is obtained. This corresponds to 61% of the theoretically obtainable amount.

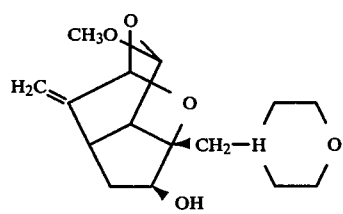

Empirical formula: $C_{15}H_{23}NO_5$
Molecular weight: 297.35
$[\alpha]_D^{22}$: +42° (in methanol)

EXAMPLE 3

Alternative preparation of 3-[4-(2-pyridyl)-1-piperazinylmethyl]-4β-hydroxy-8-methoxy-10-methylene-2,9-dioxatricyclo[4,3,1,0³,⁷] decane (XXV) from (VIII).

100 ml of dimethyl formamide are added to 38 g of (VIII), 49 g of 1-(2-pyridyl)-piperazine and 50 g of sodium hydrogen carbonate and the mixture is refluxed for 8 hours. The mixture is filtered over theorite which is then washed with methanol and the filtrate is then evaporated under vacuum. The evaporation residue is dissolved in 200 ml of methanol and a solution of 8 g of sodium hydroxide in 10 ml of water is added and the mixture is then allowed to stand at room temperature for 10 minutes. Then the mixture is neutralized with diluted hydrochloric acid, the solvent is evaporated and the residue is alkalized with 2 N sodium hydroxide solution and extracted with chloroform. The chloroform phases are treated with sodium sulfate and active carbon and then are filtered by suction over theorite. After evaporation of the chloroform, the residue is purified by chromatography over a column of silica gel using a mixture of 50% ether in n-hexane as elution solvent. After evaporating the eluate and triturating the residue with methanol, the product crystallizes. The crystalline product is filtered by suction and washed with methanol. Thus, 29.0 g of white crystals are obtained. This corresponds to 77.7% of the theoretically obtainable amount.

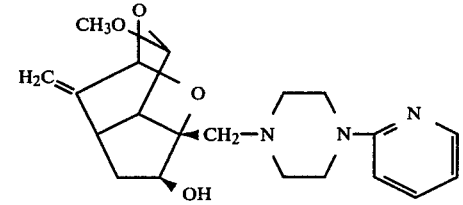

Empirical formula: $C_{20}H_{27}N_3O_4$
Molecular weight: 373.45
mp: 130°–132° C.
$[\alpha]_D^{23}$: 0° (in methanol)

EXAMPLE 4

Preparation of 3-(N,N-diethylaminomethyl)-4β-hydroxy-8-methoxy-10-methylene-2,9-dioxatricyclo[4,3,1,0³,⁷] decane (XXVI) from (VIII).

200 ml of diethylamine are added to 38 g of (VIII) and 50 g of sodium hydrogen carbonate. The reaction mixture is kept in a bomb tube at 150° C. in an oil bath for 6 hours and then is cooled to room temperature. Subsequently, a mixture of 4 g of sodium hydroxide in 10 ml of water and 100 ml of methanol is added. The mixture is allowed to stand for 10 minutes at room temperature and then 6 ml of acetic acid are added. The solvent is evaporated, the remaining mixture is covered with a layer of 100 ml of ether and then is dissolved in 200 ml of water. 40 ml of a 30% sodium hydroxide solution is added and the mixture is shaken. After separation of the etherical phase, the aqueous phase is extracted 3 times more with 100 ml ether each. The united ether extracts are dried over sodium sulfate, clarified with active carbon and filtered by suction over theorite, which is then washed with ether. The filtrate is then evaporated in a rotation evaporator first at 50° C. under reduced pressure which is produced by means of a water jet pump and subsequently at 100° C. under vacuum which is produced by means of an oil pump. Thereby 32 g of an oily product are obtained.

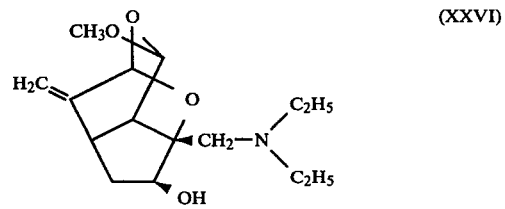

Empirical formula: $C_{15}H_{25}NO_4$
Molecular weight: 283.37
$[\alpha]_D^{23}$ = +48° (in methanol)

Analogous to Example 4, the following compounds are prepared:

3-(N,N-diethylaminomethyl)-4-oxo-8-methoxy-10-methylene-2,9-dioxatricyclo[4,3,1,0³,⁷] decane (XXVII) from 3-iodomethyl-4-oxo-8-methoxy-10-methylene-2,9-dioxatricyclo[4,3,1,0³,⁷] decane.

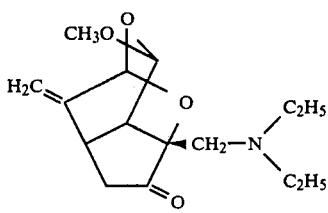

(XXVII)

Empirical formula: $C_{15}H_{23}NO_4$
Molecular weight: 281.34
3-(N,N-diethylaminomethyl)-4α-hydroxy-8-methoxy-10-methylene-2,9-dioxatricyclo[4,3,1,0$^{3,7}$] decane (XXVIII) from 3-iodomethyl-4α-hydroxy-8-methoxy-10-methylene-2,9-dioxatricyclo[4,3,1,0$^{3,7}$] decane.

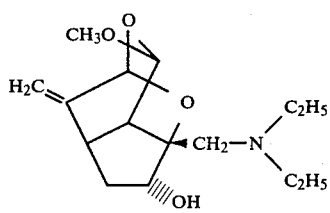

(XXVIII)

Empirical formula: $C_{15}H_{25}NO_4$
Molecular weight: 283.36

EXAMPLE 5

Preparation of 3-piperidinomethyl-4β-hydroxy-8-methoxy-10-methyl-2,9-dioxatricyclo[4,3,1,0$^{3,7}$] decane (II) from (IIa).

A hydrogenation apparatus is flushed with nitrogen for 10 minutes and then flushed with hydrogen for 10 minutes and then is filled with nitrogen.

100 g of moist Raney nickel are washed into the hydrogenation flask by means of methanol and are prehydrogenated under low excess pressure and stirring for about 2 minutes at room temperature. After introducing the solution of 180 g of the substance (IIa) in 250 ml of methanol into the hydrogenation flask, there is further washed in a mixing solution of sodium hydroxide, which is prepared by dissolving 20 g of sodium hydroxide in a small amount of water, cooling this solution to room temperature and diluting it with methanol to the five fold amount. The mixture is hydrogenated under a low excess of pressure at room temperature for about 30 minutes. After the hydrogen uptake has stopped, the mixture is filtered over theorite through a suction filter which is then washed with methanol (the catalyst must not become dry; danger of fire).

30 ml of acetic acid are added to the filtrate, the solution is evaporated at 60° C. then cooled to room temperature and the residue taken up in ether and worked into a paste with 250 ml of silica gel (particle size 0.2–0.5 mm).

After evaporation of the solvent at 50° C., the residue is taken up in a n-hexane and subsequently is evaporated at 60° C. The residue is filtered over a column of 500 g of silica gel (particle size 0.2–0.5 mm) using first 1 liter of n-hexane and then n-hexane containing 1.5% diethylamine as an eluating solvent.

After evaporation of the filtrate at 60° C., 150 g of oily (II) are obtained.

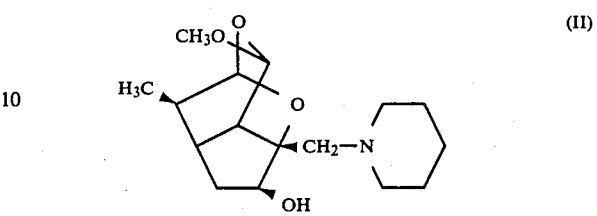

(II)

Empirical formula: $C_{16}H_{27}NO_4$
Molecular weight: 297.399
$[\alpha]_D^{23}$: 0° (in methanol)

Analogous to Example 5, the following substances are prepared (see also Table II):

3-morpholinomethyl-4β-hydroxy-8-methoxy-10-methyl-2,9-dioxatricyclo[4,3,1,0$^{3,7}$] decane (XXIX), 3-(4-methyl-1-piperazinylmethyl)-4β-hydroxy-8-methoxy-10-methyl-2,9-dioxatricyclo[4,3,1,0$^{3,7}$] decane (XXX), 3-pyrrolidinomethyl-4β-hydroxy-8α-methoxy-10α-methyl-2,9-dioxatricyclo[4,3,1,0$^{3,7}$] decane (XXXI), 3-(4-phenyl-1-piperazinylmethyl)-4β-hydroxy-8-methoxy-10-methyl-2,9-dioxatricyclo[4,3,1,0$^{3,7}$] decane (XXXII), 3-(4-hydroxyethyl-1-piperazinylmethyl)-4β-hydroxy-8-methoxy-10-methyl-2,9-dioxatricyclo[4,3,1,0$^{3,7}$] decane (XXXIII), 3-(N,N',N'-triethylethylenediaminomethyl)-4β-hydroxy-8-methoxy-10-methyl-2,9-dioxatricyclo[4,3,1,0$^{3,7}$] decane (XXXIV), 3-(N-benzyl-N-methylaminomethyl)-4β-hydroxy-8-methoxy-10-methyl-2,9-dioxatricyclo[4,3,1,0$^{3,7}$] decane (XXXV), 3-(N,N-dibenzylaminomethyl)-4β-hydroxy-8-methoxy-10-methyl-2,9-dioxatricyclo[4,3,1,0$^{3,7}$] decane (XXXVI), 3-hexamethyleneiminomethyl-4β-hydroxy-8-methoxy-10-methyl-2,9-dioxatricyclo[4,3,1,0$^{3,7}$] decane (XXXVII), 3-(1-indolinomethyl)-4β-hydroxy-8-methoxy-10-methyl-2,9-dioxatricyclo[4,3,1,0$^{3,7}$] decane (XXXVIII), 3-[4-(2-pyridyl)-1-piperazinylmethyl]-4β-hydroxy-8-methoxy-10-methyl-2,9-dioxatricyclo[4,3,1,0$^{3,7}$] decane (XXXIX), 3-pyrrolidinomethyl-4β-hydroxy-8-methoxy-10-methyl-2,9-dioxatricyclo[4,3,1,0$^{3,7}$] decane (XL), 3-piperidinomethyl-4α-hydroxy-8-methoxy-10-methyl-2,9-dioxatricyclo[4,3,1,0$^{3,7}$] decane (XLI) from 3-chloromethyl-4α-hydroxy-8-methoxy-10-methyl-2,9-dioxatricyclo[4,3,1,0$^{3,7}$] decane, 3-(N,N-diethylaminomethyl)-4β-hydroxy-8-methoxy-10-methyl-2,9-dioxatricyclo[4,3,1,0$^{3,7}$] decane (XLII), 3-(N,N-diethylaminomethyl)-4β-hydroxy-8-methoxy-10-methyl-2,9-dioxatricyclo[4,3,1,0$^{3,7}$] decane (XLIII).

TABLE II

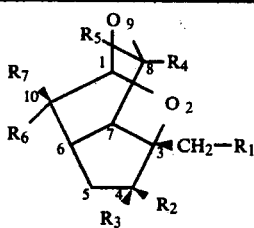

| Current Number | R₁ | R₂ | R₃ | R₄ | R₅ | R₆ | R₇ | Empirical Formula | Molecular Weight | mp °C. | $[\alpha]_D^{22}$ |
|---|---|---|---|---|---|---|---|---|---|---|---|
| XXIX | —N(morpholine) | H | OH | H | OCH₃ | H | CH₃ | $C_{15}H_{25}NO_5$ | 299.37 | <0 | 0 |
| XXX | —N(N-methylpiperazine) | H | OH | H | OCH₃ | H | CH₃ | $C_{16}H_{28}N_2O_5$ | 312.41 | <0 | 0 |
| XXXI | —N(pyrrolidine) | H | OH | OCH₃ | H | CH₃ | H | $C_{15}H_{25}NO_4$ | 283.37 | <0 | +50 |
| XXXII | —N(N-phenylpiperazine) | H | OH | H | OCH₃ | H | CH₃ | $C_{21}H_{30}N_2O_4$ | 374.48 | 143–147 | 0 |
| XXXIII | N(N-hydroxyethylpiperazine) | H | OH | H | OCH₃ | H | CH₃ | $C_{17}H_{30}N_2O_5$ | 342.44 | <0 | 0 |
| XXXIV | —N(C₂H₅)—CH₂—CH₂—N(C₂H₅)₂ | H | OH | H | OCH₃ | H | CH₃ | $C_{20}H_{36}N_2O_4$ | 368.52 | <0 | 0 |
| XXXV | —N(CH₃)—CH₂—C₆H₅ | H | OH | H | OCH₃ | H | CH₃ | $C_{19}H_{27}NO_4$ | 333.43 | <0 | 0 |
| XXXVI | —N(CH₂—C₆H₅)₂ | H | OH | H | OCH₃ | H | CH₃ | $C_{25}H_{31}NO_4$ | 403.53 | <0 | 0 |
| XXXVII | —N(piperidine) | H | OH | H | OCH₃ | H | CH₃ | $C_{17}H_{28}NO_4$ | 311.42 | <0 | 0 |
| XXXVIII | indolyl | H | OH | H | OCH₃ | H | CH₃ | $C_{18}H_{25}NO_4$ | 331.41 | <0 | 0 |
| XXXIX | —N(N-(2-pyridyl)piperazine) | H | OH | H | OCH₃ | H | CH₃ | $C_{20}H_{28}N_3O_4$ | 375.47 | 175–177 | 0 |
| XL | —N(pyrrolidine) | H | OH | H | OCH₃ | H | CH₃ | $C_{15}H_{25}NO_4$ | 283.37 | <0 | 0 |
| XLI | —N(piperidine) | OH | H | H | OCH₃ | H | CH₃ | $C_{16}H_{27}NO_4$ | 297.39 | <0 | 0 |

TABLE II-continued

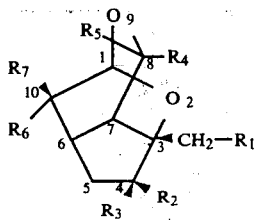

| Current Number | R₁ | R₂ | R₃ | R₄ | R₅ | R₆ | R₇ | Empirical Formula | Molecular Weight | mp °C. | $[\alpha]_D^{22}$ |
|---|---|---|---|---|---|---|---|---|---|---|---|
| XLII | −N(C₄H₈)(C₄H₈) | H | OH | H | OCH₃ | H | CH₃ | $C_{18}H_{35}NO_4$ | 341.48 | <0 | +12.4 |
| XLII | −N(C₂H₅)(C₂H₅) | H | OH | H | OCH₃ | H | CH₃ | $C_{15}H_{27}NO_4$ | 285.38 | <0 | 0 |

EXAMPLE 6

Preparation of 3-(N-methylaminomethyl)-4β-hydroxy-8-methoxy-10-methyl-2,9-dioxatricyclo[4,3,1,0³,⁷] decane monohydrate (XLIV).

16.9 g of 3-(N-benzyl-N-methylaminomethyl)4β-hydroxy-8-methoxy-10-methyl-2,9-dioxatricyclo[4,3,1,0³,⁷] decane are dissolved in ethanol and hydrogenated with hydrogen in the presence of 5 g of palladium oxide. Duration of the hydrogenation: 2 hours. After the hydrogen uptake has stopped the reaction mixture is filtered over theorite through a suction filter which then is washed with ethanol. After evaporating the filtrate the residue is crystallized from chloroform/ether and 11 g of the debenzylated compound are obtained, corresponding to 84% of theoretical amount. The crystals are washed with ether and air dried.

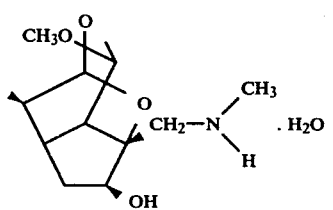
(XLIV)

Empirical formula: $C_{12}H_{21}NO_4 + H_2O$
Molecular weight: 261.30
$[\alpha]_D^{22}$: −25° in methanol

EXAMPLE 7

Preparation of 3-piperidinomethyl-4β-phenylcarbamoyloxy-8-methoxy-10-methyl-2,9-dioxatricyclo[4,3,1,0³,⁷] decane (XLV) from (II).

5.0 g of (II) are dissolved in 10 ml of methylene chloride. 3 ml of phenyl isocyanate and 680 mg of phenylmercury acetate as a catalyst are added and subsequently the reaction mixture is reflexed for 1 to 2 hours. After adding 5 ml of methanol the mixture is evaporated. The residue is dissolved in ether and treated with sodium sulfate and active carbon. After filtering the mixture, washing the filter residue with ether and evaporating the filtrate, 6.27 g of the crystalline phenyl carbonate are obtained. This corresponds to 90% of the theoretically obtainable amount.

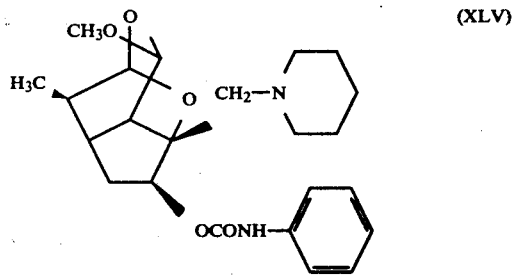
(XLV)

Empirical formula: $C_{23}H_{32}N_2O_5$
Molecular weight: 416.52
mp: 81°-86° C.

Analogous to Example 7, the following substances are prepared (see also Table III):

3-hexamethyleneiminomethyl-4β-ethylcarbamoyloxy-8-methoxy-10-methylene-2,9-dioxatricyclo[4,3,1,0³,⁷] decane (XLVI), 3-[4-(p-chlorbenzhydryl)-1-piperazinylmethyl]-4β-ethylcarbamoyl-8-methoxy-10-methylene-2,9-dioxatricyclo[4,3,1,0³,⁷] decane (XLVII), 3-(4-methyl-1-piperazinylmethyl)-4β-phenylcarbamoyloxy-8-methoxy-10-methylene-2,9-dioxatricyclo[4,3,1,0³,⁷] decane (XLVIII), 3-[4-(2-ethylcarbamoyloxyethyl)-1-piperazinylmethyl]-4β-ethylcarbamoyloxy-8-methoxy-10-methyl-2,9-dioxatricyclo[4,3,1,0³,⁷] decane (XLIX), 3-[4-pyridyl-2)-1-piperazinylmethyl]-4β-ethylcarbamoyloxy-8-methoxy-10-methylene-2,9-dioxatricyclo[4,3,1,0³,⁷] decane (L), 3-(4-methyl-1-piperazinylmethyl)-4β-ethylcarbamoyloxy-8-methoxy-10-methylene-2,9-dioxatricyclo[4,3,1,0³,⁷] decane (LI), 3-(N,N′,N′-triethylenediaminomethyl)-4β-ethylcarbamoyl-8-methoxy-10-methyl-2,9-dioxatricyclo[4,3,1,0³,⁷] decane (LII), 3-pyrrolidinomethyl-4β-isopropylcarbamoyloxy-8-methoxy-10-methylene-2,9-dioxatricyclo[4,3,1,0³,⁷] decane (LIII), 3-piperidinomethyl-4α-allylcarbamoyloxy-8-methoxy-10-methyl-2,9-dioxatricyclo[4,3,1,0³,⁷] decane (LIV), 3-piperidinomethyl-4α-isopropylcarbamoyloxy-8-methoxy-10-methyl-2,9-dioxatricyclo[4,3,1,0^{3,7}] decane (LV), 3-piperidinomethyl-4β-ethylcarbamoyloxy-8-methoxy-10-methylene-2,9-dioxatricyclo[4,3,1,0^{3,7}] decane (LVI), 3-piperidinomethyl-4β-isopropylcarbamoyloxy-8-methoxy-10-methylene-2,9-dioxatricyclo[4,3,1,0^{3,7}] decane (LVII), 3-(N,N-diethylaminoethyl)-4β-allylcarbamoyloxy-8-methoxy-10-methylene-2,9-dioxatricyclo[4,3,1,0^{3,7}] decane (LVIII), 3-piperidinomethyl-4β-allylcarbamoyloxy-8-methoxy-10-methylene-2,9-dioxatricyclo[4,3,1,0^{3,7}] decane (LIX).

TABLE III

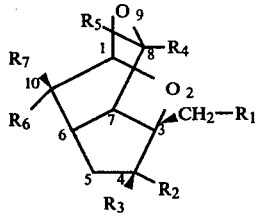

| Current Number | $R_1$ | $R_2$ | $R_3$ | $R_4$ | $R_5$ | $R_6$ |
|---|---|---|---|---|---|---|
| XLVI | –N(piperidine) | H | $OCONH-C_2H_5$ | H | $OCH_3$ | — |
| XLVII | –N(piperazine)N–C–H, phenyl | H | $OCONH-C_2H_5$ | H | $OCH_3$ | — |
| | phenyl-CH | | | | | |
| XLVIII | –N(piperazine)N–$CH_3$ | H | OCONH–phenyl | H | $OCH_3$ | — |
| XLIX | –N(piperazine)N–$CH_2$–CH($CH_2$–$C_2H_5$)(NH–CO) | H | $OCONH-C_2H_5$ | H | $OCH_3$ | H |
| L | –N(piperazine)N–(pyridyl) | H | $OCONH-C_2H_5$ | H | $OCH_3$ | — |
| LI | –N(piperazine)N–$CH_3$ | H | $OCONH-C_2H_5$ | H | $OCH_3$ | — |
| LII | $-N(C_2H_5)-CH_2-CH_3-N(C_2H_5)(C_2H_5)$ | H | $OCONH-C_2H_5$ | H | $OCH_3$ | H |
| LIII | –N(pyrrolidine) | H | $OCONH-CH(CH_3)_2$ | H | $OCH_3$ | — |
| LIV | –N(piperidine) | $OCONH-CH_2-CH=CH_2$ | H | H | $OCH_3$ | H |
| LV | –N(piperidine) | $OCONH-CH(CH_3)_2$ | $CH_3$ | H | $OCH_3$ | H |
| LVI | –N(piperidine) | H | $OCONH-C_2H_5$ | H | $OCH_3$ | — |

TABLE III-continued

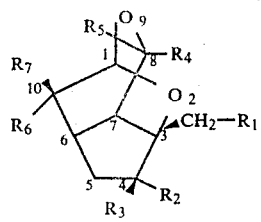

| | | R7 | R6 + R7 | | | |
|---|---|---|---|---|---|---|
| LVII | –N⟨piperidine⟩ | H | OCONH—CH(CH₃)₂ | H | OCH₃ | — |
| LVIII | –N⟨piperidine⟩ | H | OCONH—CH₂—CH=CH₂ | H | OCH₃ | — |
| LIX | –N(C₂H₅)₂ | OCONH—CH₂—CH—CH₂ | H | H | OCH₃ | — |

| | Current Number | R₇ | R₆ + R₇ | Empirical Formula | Molecular Weight | mp °C. | $[\alpha]_D^{22}$ |
|---|---|---|---|---|---|---|---|
| | XLVI | — | CH₂ | C₂₀H₃₂N₂O₅ | 380.48 | 42–47 | +22 |
| | XLVII | — | CH₂ | C₃H₃₈N₃ClO₅ | 568.08 | <0° | |
| | XLVIII | — | CH₂ | C₂₃H₃₂N₃O₅ | 430.51 | 156–160 | |
| | XLIX | CH₃ | — | C₂₃H₄₀N₄O₇ | 484.38 | <0° | |
| | L | — | CH₂ | C₂₃H₃₂N₄O₅ | 444.52 | | +30 |
| | LI | — | CH₂ | C₁₉H₃₁N₃O₅ | 381.46 | | +38 |
| | LII | CH₃ | — | C₂₃H₄₁N₃O₅ | 439.58 | <0 | |
| | LIII | — | CH₂ | C₁₉H₃₀N₂O₅ | 366.46 | 123–125 | +29 |
| | LIV | CH₃ | — | C₂₀H₃₂N₂O₅ | 380.48 | <0 | |
| | LV | CH₃ | — | C₂₀H₃₄N₂O₅ | 382.49 | <0 | |
| | LVI | — | CH₂ | C₁₈H₃₀N₂O₅ | 366.45 | <0 | |
| | LVII | — | CH₂ | C₂₀H₃₂N₂O₅ | 380.48 | <0 | |
| | LVIII | — | CH₂ | C₂₀H₃₀N₂O₅ | 378.46 | <0 | |
| | LIX | — | CH₂ | C₁₉H₃₀N₂O₅ | 366.45 | <0 | |

EXAMPLE 8

Preparation of 3-morpholinomethyl-4β-benzoyloxy-8-methoxy-10-methyl-2,9-dioxatricyclo[4,3,1,0³,⁷] decane (LX) from (V).

3.73 g of (V) are dissolved in pyridine. 7.05 g of benzoic acid anhydride are added and the mixture is refluxed for 2 hours. After adding chloroform, the mixture is shaken with a 2 N solution of sodium carbonate. The organic phase is separated and washed with water once. The aqueous phases are separately extracted with chloroform twice each. The united organic extracts are treated with sodium sulfate and active carbon and filtered over theorite. After evaporating the filtrate, the residue is purified by column chromatography over silica gel using a mixture of 50% of ether in n-hexane as an eluating liquid. After evaporating the eluate, 2.9 g of the benzoate are crystallized from isopropanol. This corresponds to 57% of the theoretically obtainable amount.

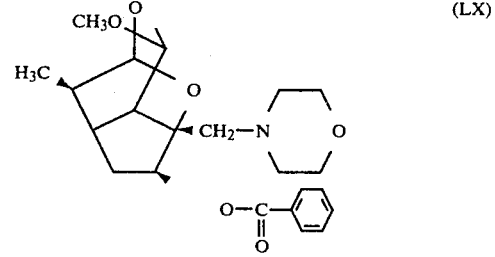

(LX)

Empirical formula: C₂₂H₂₉NO₆
Molecular weight: 403.45
mp: 120°–121° C.
$[\alpha]_D^{22}$: +60° in methanol Analogous to Example 8, the following substances are prepared:

3-[4-pyridyl-2)-1-piperazinylmethyl]-4β-benzoyloxy-8-methoxy-10-methylene-2,9-dioxatricyclo[4,3,1,0³,⁷] decane (LXI)

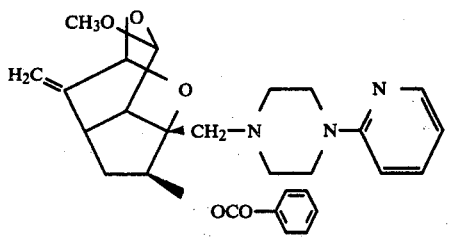

(LXI)

Empirical formula: $C_{27}H_{31}N_3O_5$
Molecular weight: 477.54
3-(4-methyl-1-piperazinylmethyl)-4β-benzoyloxy-8-methoxy-10-methylene-2,9-dioxatricyclo[4,3,1,0$^{3,7}$] decane (LXII)

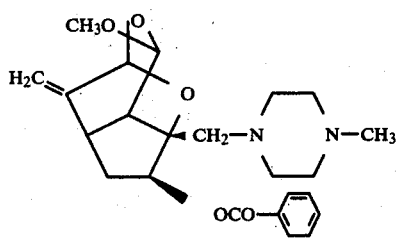

(LXII)

Empirical formula: $C_{23}H_{31}N_2O_5$
Molecular weight: 416.09
mp: 99°-102° C.
3-[4-(2-benzoyloxyethyl)-1-piperazinylmethyl]-4β-benzoyloxy-8-methoxy-10-methyl-2,9-dioxatricyclo[4,3,1,0$^{3,7}$] decane (LXIII)

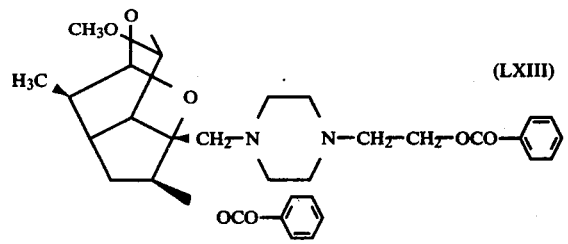

(LXIII)

Empirical formula: $C_{31}H_{38}N_2O_7$
Molecular weight: 550.63

EXAMPLE 9

Preparation of 3-hexamethyleneiminomethyl-4β-acetoxy-8-methoxy-10-methyl-2,9-dioxatricyclo[4,3,1,0$^{3,7}$] decane (LXIV) from 3-hexamethyleneiminomethyl-4β-hydroxy-8-methoxy-10-methyl-2,9-dioxatricyclo[4,3,1,0$^{3,7}$] decane.

3 g of 3-hexamethyleneiminomethyl-4β-hydroxy-8-methoxy-10-methyl-2,9-dioxatricyclo[4,3,1,0$^{3,7}$] decane are dissolved in 6 ml of acetic anhydride and the mixture is allowed to stand for 30 minutes at room temperature. After adding chloroform, the mixture is shaken with a 2 N solution of sodium carbonate. The organic phase is separated and washed with water once. Both the aqueous phases are extracted with chloroform twice each.

The united organic extracts are treated with sodium sulfate and active carbon. After filtering by suction and evaporating the filtrate, the residue is purified by column chromatography over aluminum oxide using as an eluating liquid first a mixture of 50% of ether in n-hexane, then ether only and finally ether which contains 10% of methanol. After evaporating the eluate, 2.2 g of the oily acetate are obtained which corresponds to 67.8% of the theoretically obtainable amount.

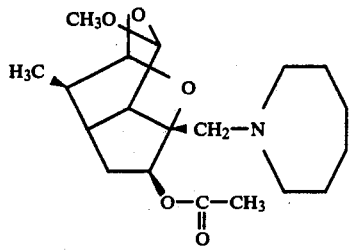

(LXIV)

Empirical formula: $C_{19}H_{31}NO_5$
Molecular weight: 337.44
$[\alpha]_D^{22}$: ±0° in methanol

EXAMPLE 10

Preparation of 3-hexamethyleneiminomethyl-4β-propionyloxy-8-methoxy-10-methyl-2,9-dioxatricyclo[4,3,1,0$^{3,7}$] decane (LXV).

2.74 g of 3-hexamethyleneiminomethyl-4β-hydroxy-8-methoxy-10-methyl-2,9-dioxatricyclo[4,3,1,0$^{3,7}$] decane are dissolved in 6 ml of propionic acid anhydride and the mixture is allowed to stand for 30 minutes at room temperature. After adding chloroform, the mixture is shaken with a 2 N solution of sodium carbonate. The organic phase is separated and treated with sodium sulfate and active carbon. After filtering and evaporating the filtrate, 950 mg of the propionate are obtained, which crystallize from isopropanol. This corresponds to 29.4% of the theoretically obtainable amount.

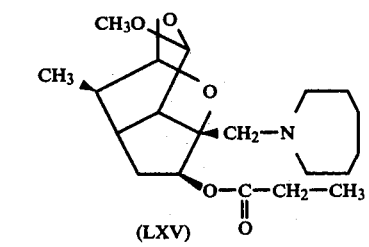

(LXV)

Empirical formula: $C_{20}H_{33}NO_5$
Molecular weight: 367.47
mp: 52°-54° C.
$[\alpha]_D^{22}$: ±0° in methanol Analogous to Example 10, the following substance is prepared:
3-[4-(p-chlorbenzhydryl)-1-piperazinylmethyl]-4β-propionyloxy-8-methoxy-10-methylene-2,9-dioxatricyclo[4,3,1,0$^{3,7}$] decane (LXVI).

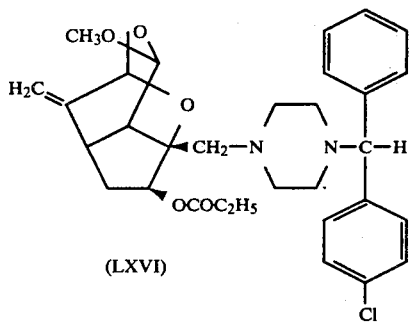

(LXVI)

Empirical formula: C31H37N2ClO5
Molecular weight: 552.78

EXAMPLE 11

Preparation of 3-piperidinomethyl-4β-hydroxy-8-methoxy-10-methyl-2,9-dioxatricyclo[4,3,1,0$^{3,7}$] decane hydrochloride (LXVII) from (II).

5 g of (II) are dissolved in 50 ml of ether. Dry gaseous hydrogen chloride is passed through the solution, until no further precipitate is formed. The ether is decanted and the precipitate is triturated with another portion of ether which is free from hydrogen chloride. After filtering the precipitate by suction, washing it with ether and drying it, 5.4 g of the crystalline hydrochloride are obtained. This corresponds to 97% of the theoretically obtainable amount.

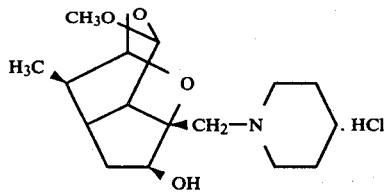

(LXVII)

Empirical formula: C16H28NClO4
Molecular weight: 333.86
mp: 182°–188° C.
[α]$_D^{22}$: −18° C. in methanol Analogous to Example 11, the following substances are prepared (see also Table IV).

3-pyrrolidinomethyl-4β-hydroxy-8-methoxy-10-methyl-2,9-dioxatricyclo[4,3,1,0$^{3,7}$] decane hydrochloride (LXVIII), 3-morpholinomethyl-4β-hydroxy-8-methoxy-10-methyl-2,9-dioxatricyclo[4,3,1,0$^{3,7}$] decane hydrochloride (LXIX), 3-(4-phenyl-1-piperazinylmethyl)-4β-hydroxy-8-methoxy-10-methyl-2,9-dioxatricyclo[4,3,1,0$^{3,7}$] decane dihydrochloride (LXX), 3-hexamethyleneiminomethyl-4β-hydroxy-8-methoxy-10-methylene-2,9-dioxatricyclo[4,3,1,0$^{3,7}$] decane hydrochloride (LXXI), 3-piperidinomethyl-4β-phenylcarbamoyloxy-8-methoxy-10-methyl-2,9-dioxatricyclo[4,3,1,0$^{3,7}$] decane hydrochloride (LXXII), 3-hexamethyleneiminomethyl-4β-hydroxy-8-methoxy-10-methyl-2,9-dioxatricyclo[4,3,1,0$^{3,7}$] decane hydrochloride (LXXIII), 3-(1-indolinomethyl)-4β-hydroxy-8-methoxy-10-methylene-2,9-dioxatricyclo[4,3,1,0$^{3,7}$] decane hydrochloride (LXXIV), 3-(1-indolinomethyl)-4β-hydroxy-8-methoxy-10-methyl-2,9-dioxatricyclo[4,3,1,0$^{3,7}$] decane hydrochloride (LXXV), 3-[4-(p-chlorobenzhydryl)-1-piperazinylmethyl]-4β-äthylcarbamoyloxy-8-methoxy-10-methylene-2,9-dioxatricyclo[4,3,1,0$^{3,7}$] decane dihydrochloride (LXXVI).

TABLE IV

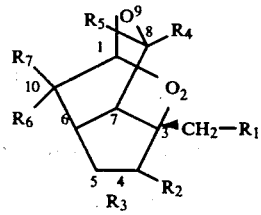

| Current Number | R$_1$ | R$_2$ | R$_3$ | R$_4$ | R$_5$ | R$_6$ |
|---|---|---|---|---|---|---|
| LXVIII | —N⟩ . HCl | H | OH | H | OCH$_3$ | H |
| LXIX | —N⟩O . HCl | H | OH | H | OCH$_3$ | H |

TABLE IV-continued

| | | R1 | R2 | R3 | R4 | R5 |
|---|---|---|---|---|---|---|
| LXX | —N⟩N—⟨O⟩ . 2HCO | H | OH | H | OCH3 | H |
| LXXI | —N⟩ . HCl | H | OH | H | OCH3 | — |
| LXXII | —N⟩ . HCl | H | OCONH—⟨O⟩ | H | OCH3 | H |
| LXXIII | —N⟩ . HCl | H | OH | H | OCH3 | H |
| LXXIV | indoline . HCl | H | OH | H | OCH3 | — |
| LXXV | indoline . HCl | H | OH | H | OCH3 | H |
| LXXVI | —N⟩N—CH(⟨O⟩)(⟨O⟩Cl) . 2HCl | H | OCONH—C2H5 | H | OCH3 | — |

| Current Number | R7 | R6 + R7 | Empirical Formula | Molecular Weight | mp °C. | $[\alpha]_D^{22}$ |
|---|---|---|---|---|---|---|
| LXVIII | CH3 | — | C15H26NClO4 | 319.83 | 198–204 | −13 |
| LXIX | CH3 | — | C15H26NClO5 | 333.83 | 175–180 | −28 |
| LXX | CH3 | — | C21H32N2Cl2O4 | 447.40 | 148–150 | −36 |
| LXXI | — | CH2 | C17H28NClO4 | 345.87 | 220–230 | 0 |
| LXXII | CH3 | — | C23H33N2ClO5 | 452.98 | 240–250 | 0 |
| LXXIII | CH3 | — | C17H30NClO4 | 347.88 | 184–188 | 0 |
| LXXIV | — | CH2 | C18H24NClO4 | 365.85 | 200–205 | 0 |
| LXXV | CH3 | — | C18H26NClO4 | 367.67 | 140–150 | 0 |
| LXXVI | — | CH2 | C31H40N3Cl3O5 | 641.02 | 350 | +18 |

EXAMPLE 12

Preparation of 3-pyrrolidinomethyl-4β-hydroxy-8-methoxy-10-methylene-2,9-dioxatricyclo[4,3,1,0$^{3,7}$]decane hydrogenmaleinate (LXXVII) from (IV).

3.3. g of (IV) are dissolved in 20 ml of ether and a solution of 1.4 g of maleic acid in ether is added. After decanting the solvent, the residue is triturated with another portion of ether. After filtering the residue by suction, washing it with ether and drying, 4.4 g of the maleinate are obtained. This corresponds to 90.2% of the theoretically obtainable amount.

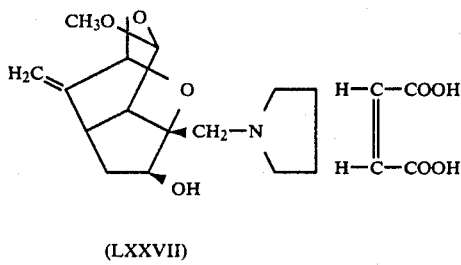

(LXXVII)

Empirical formula: $C_{19}H_{27}NO_8$

Molecular weight: 397.43
mp: 155°–157° C.
$[\alpha]_D^{22}$: +8° C. in methanol

Analogous to Example 12, the following substances are prepared (see also Table V):

3-(4-methyl-1-piperazinylmethyl)-4β-hydroxy-8-methoxy-10-methyl-2,9-dioxatricyclo[4,3,1,0$^{3,7}$] decane dihydrogenmaleinate (LXXVIII), 3-pyrrolidinomethyl-4β-hydroxy-8α-methoxy-10-methyl-2,9-dioxatricyclo[4,3,1,0$^{3,7}$] decane hydrogenmaleinate (LXXIX), 3-[4-(p-chlorbenzhydryl)-1-piperazinylmethyl]-b 4β-ethylcarbamoyloxy-8-methoxy-10-methylene-2,9-dioxatricyclo[4,3,1,0$^{3,7}$] decane dihydrogenmaleinate (LXXX), 3-(4-methyl-1-piperazinylmethyl)-4β-phenylcarbamoyloxy-8-methoxy-10-methylene-2,9-dioxatricyclo[4,3,1,0$^{3,7}$] decane dihydrogenmaleinate (LXXXI), 3-[4-(2-hydroxyethyl)-1-piperazinylmethyl]-4β-hydroxy-8-methoxy-10-methyl-2,9-dioxatricyclo[4,3,1,0$^{3,7}$] decane dihydrogenmaleinate (LXXXII).

TABLE V

| Current Number | $R_1$ | n | $R_2$ | $R_3$ | $R_4$ | $R_5$ | $R_6$ |
|---|---|---|---|---|---|---|---|
| LXXVIII | −N⟨piperazinyl⟩N−CH₃ | 2 | H | OH | H | OCH₃ | H |
| LXXIX | −N⟨pyrrolidinyl⟩ | 1 | H | OH | OCH₃ | H | CH₃ |
| LXXX | −N⟨piperazinyl⟩N−CH(C₆H₅)(C₂H₄Cl) | 2 | H | OCONHC₂H₅ | H | OCH₃ | — |
| LXXXI | −N⟨piperazinyl⟩N−CH₃ | 2 | H | OCONH−C₆H₅ | H | OCH₃ | — |
| LXXXII | −N⟨piperazinyl⟩N−CH₂CH₂−OH | 2 | H | OH | H | OCH₃ | H |

| Current Number | $R_7$ | $R_6 + R_7$ | Empirical Formula | Molecular Weight | mp °C. | $[\alpha]_D^{22}$ |
|---|---|---|---|---|---|---|
| LXXVIII | CH₃ | — | $C_{24}H_{36}N_2O_{12}$ | 544.56 | 151–154 | −4° |
| LXXIX | H | — | $C_{19}H_{29}NO_8$ | 399.45 | 135–145 | +36° |
| LXXX | — | CH₂ | $C_{39}H_{46}N_3ClO_{13}$ | 800.24 | | +15° |
| LXXXI | — | CH₂ | $C_{31}H_{40}N_3O_{13}$ | 662.65 | 82–91 | |
| LXXXII | CH₃ | — | $C_{21}H_{34}N_2O_9$ | 458.51 | 133–135 | |

EXAMPLE 13

Preparation of 3-piperidinomethyl-4β-hydroxy-8-methoxy-10-methyl-2,9-dioxatricyclo[4,3,1,0$^{3,7}$] decane hydrogentartrate (LXXXIII) from (II).

150 g of (II) are dissolved in 150 ml of ether then 75.0 g of a solution of L(+)-tartaric acid in ethanol is added, which is prepared by dissolving 75.0 g of L(+)-tartaric acid in 525.35 ml of ethanol at about 60° C.

The solution which in the beginning is clear, is evaporated at 60° C. whereby the hydrogen tartrate of (II) crystallizes. After evaporation of the solvent, ether is added, the crystals are filtered off through a suction filter and washed with ether. After drying at 50° C. under vacuum, 203.6 g of the white crystalline hydrogen-tartrate of (II) are obtained. This corresponds to 91% of the theoretically obtainable amount.

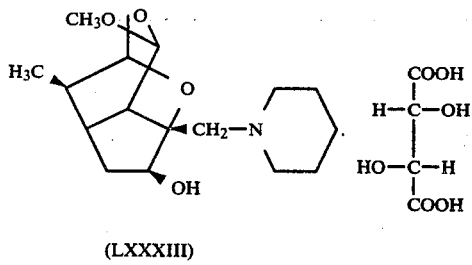

(LXXXIII)

Empirical formula: $C_{20}H_{33}NO_{10}$
Molecular weight: 447.46
mp: 178° C. (not corrected, determined on a Kofler apparatus)
$[\alpha]_D^{20}$: −5.4° in water Analogous to Example 13, the following substances are prepared (see also Table VI):

3-[4-(p-chlorbenzhydryl)-1-piperazinylmethyl]-4β-hydroxy-8-methoxy-10-methylene-2,9-dioxatricyclo[4,3,1,0$^{3,7}$] decane dihydrogentartrate (LXXXIV), 3-[4-(p-chlorbenzhydryl)-1-piperazinylmethyl]-4β-ethylcarbamoyloxy-8-methoxy-10-methylene-2,9-dioxatricyclo[4,3,1,0$^{3,7}$] decane dihydrogentartrate (LXXXV), 3-[4-(p-chlorobenzhydryl)-1-piperazinylmethyl]-4β-propionyloxy-8-methoxy-10-methylene-2,9-dioxatricyclo[4,3,1,0$^{3,7}$] decane dihydrogentartrate (LXXXVI), 3-[4-(2-pyridyl)-1-piperazinylmethyl]-4β-benzoyloxy-8-methoxy-10-methylene-2,9-dioxatricyclo[4,3,1,0$^{3,7}$] decane trihydrogentartrate (LXXXVII), 3-(4-methyl-1-piperazinylmethyl)-4β-benzoyloxy-8-methoxy-10-methylene-2,9-dioxatricyclo[4,3,1,0$^{3,7}$] decane dihydrogentartrate (LXXXVIII), 3-[4-(2-ethylcarbamoyloxyethyl)-1-piperazinylmethyl]-4β-ethyl-carbamoyloxy-8-methoxy-10-methyl-2,9-dioxatricyclo[4,3,1,0$^{3,7}$] decane dihydrogentartrate (LXXXIX), 3-(N,N',N'-triethyl-ethylenediaminomethyl)-4β-äthyl-carbamoyloxy-8-methoxy-10-methyl-2,9-dioxatricyclo[4,3,1,0$^{3,7}$] decane dihydrogentartrate (XC), 3-piperidinomethyl-4α-hydroxy-8-methoxy-10-methyl-2,9-dioxatricyclo[4,3,1,0$^{3,7}$] decane hydrogentartrate (XCI), 3-piperidinomethyl-4α-isopropylcarbamoyloxy-8-methoxy-10-methyl-2,9-dioxatricyclo[4,3,1,0$^{3,7}$] decane hydrogentartrate (XCII), 3-N,N-diethylaminomethyl-4α-hydroxy-8-methoxy-10-methylene-2,9-dioxatricyclo[4,3,1,0$^{3,7}$] decane hydrogentartrate (XCIII), 3-piperidinomethyl-4α-allylcarbamoyloxy-8-methoxy-10-methyl-2,9-dioxatricyclo[4,3,1,0$^{3,7}$] decane hydrogentartrate (XCIV), 3-N,N-diethylaminomethyl-4α-allylcarbamoyloxy-8-methoxy-10-methylene-2,9-dioxatricyclo[4,3,1,0$^{3,7}$] decane hydrogentartrate (XCV), 3-N,N-diethylaminomethyl-4-oxo-8-methoxy-10-methylene-2,9-dioxatricyclo[4,3,1,0$^{3,7}$] decane hydrogentartrate (XCVI), 3-morpholinomethyl-4β-hydroxy-8-methoxy-10-methyl-2,9-dioxatricyclo[4,3,1,0$^{3,7}$] decane hydrogentartrate (XCVII), 3-piperidinomethyl-4β-hydroxy-8-methoxy-10-methylene-2,9-dioxatricyclo[4,3,1,0$^{3,7}$] decane hydrogentartrate (XCVIII), 3-pyrrolidinomethyl-4β-hydroxy-8-methoxy-10-methyl-2,9-dioxatricyclo[4,3,1,0$^{3,7}$] decane hydrogentartrate (XCIX), 3-N,N-dibutylaminomethyl-4β-hydroxy-8-methoxy-10-methyl-2,9-dioxatricyclo[4,3,1,0$^{3,7}$] decane hydrogentartrate (C).

TABLE VI

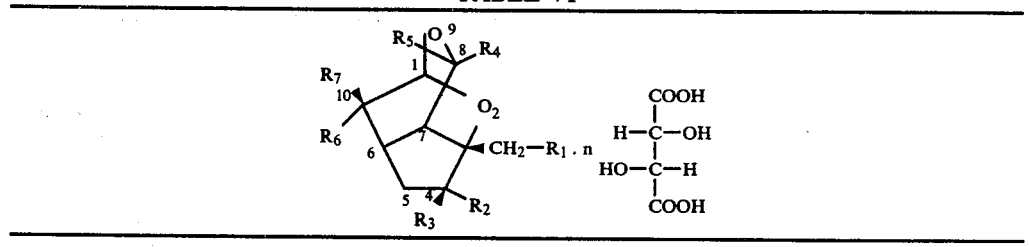

| Current Number | $R_1$ | $R_2$ | $R_3$ | $R_4$ | $R_5$ | $R_6$ | $R_7$ |
|---|---|---|---|---|---|---|---|
| LXXXIV | −N(piperazine)N−CH(C$_6$H$_5$)(C$_6$H$_4$−Cl) | H | OH | H | OCH$_3$ | — | — |
| LXXV | N(piperazine)N−CH(C$_6$H$_5$)(C$_6$H$_4$−Cl) | H | OCONHC$_2$H$_5$ | H | OCH$_3$ | — | — |
| LXXXVI | N(piperazine)N−CH(C$_6$H$_5$)(C$_6$H$_4$−Cl) | H | OCOC$_2$H$_5$ | H | OCH$_3$ | — | — |

TABLE VI-continued

| | CH₂-R₁ group | | R₂ | R₃ | R₄ | R₅ | R₆ | R₇ |
|---|---|---|---|---|---|---|---|---|
| LXXXVII | piperazinyl-pyridyl | | H | OCO— | | H | OCH₃ | — | — |
| LXXXVIII | 4-methylpiperazinyl | | H | OCO— | | H | OCH₃ | — | — |
| LXXXIX | N-piperazinyl-CH₂CH₂—OCO—N(C₄H₅)₄ | | H | OCONHC₂H₅ | H | OCH₃ | H | CH₃ |
| XC | (C₂H₅)₂N—CH₂—CH₂—N(C₂H₅)₂ | | H | OCONH—C₂H₅ | H | OCH₃ | H | CH₃ |
| XCI | piperidinyl | | OH | H | H | OCH₃ | H | CH₃ |
| XCII | piperidinyl | | OCONH—CH(CH₃)₂ | H | H | OCH₃ | H | CH₃ |
| XCIII | N(C₂H₅)₂ | | OH | H | H | OCH₃ | — | — |
| XCIV | piperidinyl | | OCONH—CH₂—CH=CH₂ | H | H | OCH₃ | H | CH₃ |
| XCV | N(C₂H₅)₂ | | OCONH—CH₂—CH=CH₂ | H | H | OCH₃ | — | — |
| XCVII | morpholinyl | | H | OH | H | OCH₃ | H | CH₃ |
| XCVIII | piperidinyl | | H | OH | H | OCH₃ | — | — |
| XCIX | pyrrolidinyl | | H | OH | H | OCH₃ | H | CH₃ |
| C | N(C₄H₉)₂ | | H | OH | H | OCH₃ | H | CH₃ |
| XCVI | N(C₂H₅)₂ | | +R₃ = O | — | H | OCH₃ | — | — |

Current    Empirical    Molecular    mp

TABLE VI-continued

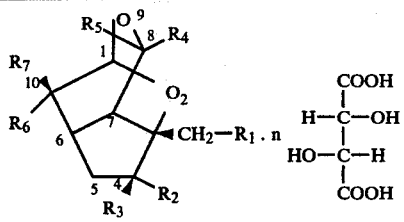

| Number | $R_6 + R_7$ | Formula | Weight | °C. | $[\alpha]_D^{22}$ | n |
|---|---|---|---|---|---|---|
| LXXXIV | $CH_2$ | $C_{36}H_{45}N_2ClO_{16}$ | 797.19 | amorphous | +10 | 2 |
| LXXV | $CH_2$ | $C_{39}H_{50}N_3ClO_{17}$ | 868.26 | amorphous | +14° | 2 |
| LXXXVI | $CH_2$ | $C_{29}H_{49}N_2ClO_{12}$ | 853.25 | amorphous | +16° | 2 |
| LXXXVII | $CH_2$ | $C_{39}H_{49}N_3O_{23}$ | 927.80 | amorphous | +28 | 3 |
| LXXXVIII | $CH_2$ | $C_{31}H_{43}N_2O_{12}$ | 715.67 | amorphous |  | 2 |
| LXXXIX | — | $C_{31}H_{52}N_4O_{19}$ | 784.77 | 88–93 |  | 2 |
| XC | — | $C_{31}H_{57}N_3O_{18}$ | 775.78 | 68–70 | 0° | 2 |
| XCI | — | $C_{20}H_{33}NO_{10}$ | 447.47 | amorphous | −25 | 1 |
| XCII | — | $C_{24}H_{40}N_2O_{11}$ | 532.58 | 93–95 | +17 | 1 |
| XCIII | $CH_2$ | $C_{19}H_{31}NO_{10}$ | 433.45 | 42–47 | +22 | 1 |
| XCIV | — | $C_{24}H_{38}N_2O_{11}$ | 530.56 | 121–123 | 0° | 1 |
| XCV | $CH_2$ | $C_{23}H_{36}N_2O_{11}$ | 516.54 | 42–45 | +44 | 1 |
| XCVII | — | $C_{19}H_{31}NO_{11}$ | 449.46 | 87 | 0° | 1 |
| XCVIII | $CH_2$ | $C_{20}H_{31}NO_{10}$ | 445.48 | 187 | +25.5° | 1 |
| XCIX | — | $C_{19}H_{31}NO_{10}$ | 433.45 | 148–160 | 0° | 1 |
| C | — | $C_{23}H_{42}NO_{10}$ | 481.58 | 135 |  | 1 |
| XCVI | $CH_2$ | $C_{18}H_{29}NO_{10}$ | 431.43 | amorphous | +19° | 1 |

EXAMPLE 15

A. Preparation of 3-iodomethyl-4β-hydroxy-8-methoxy-10-methylene-2,9-dioxatricyclo[4,3,1,0$^{3,7}$] decane (CIV) from 3-iodomethyl-4β-acetoxy-8-methoxy-10-methylene-2,9-dioxatricyclo[4,3,1,0$^{3,7}$] decane (VIII).

To a solution of 38 g of (VIII) in 250 ml of methanol 4 g of sodium hydroxide in 50 ml of methanol are added and the mixture is stirred at room temperature for 30 minutes.

500 ml of water are added and the mixture then is neutralized with glacial acid, saturated with ammonium sulfate and extracted with ether. The united organic phases are dried over sodium sulfate, filtered and the residue is washed with ether. The filtrate is then evaporated under vacuum at 50° C. 36.64 g of a colorless oil are obtained. This corresponds to 94.5% of the theoretically obtainable amount.

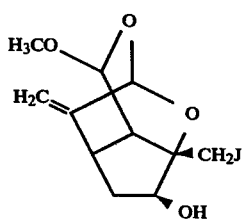

(CIV)

Empirical formula: $C_{11}H_{15}O_4J$
Molecular weight: 338.15
$[\alpha]_D^{22}$: +13° in methanol B. Preparation of 3-iodomethyl-4β-hydroxy-8-methoxy-10-methyl-2,9-dioxatricyclo[4,3,1,0$^{3,7}$] decane (CV) from 3-iodomethyl-4β-hydroxy-8-methoxy-10-methylene-2,9-dioxatricyclo[4,3,1,0$^{3,7}$] decane (CIV).

To 75 g of 3-iodomethyl-4β-hydroxy-8-methoxy-10-methylene-2,9-dioxatricyclo[4,3,1,0$^{3,7}$] decane in 250 ml of ethanol 6 g of platinum (IV) oxide in 100 ml of ethanol are added and the mixture is hydrogenated at room temperature (hydrogen uptake 5 liters). After sucking off the catalyst, the solution is evaporated in a rotation evaporator at 50° C. The residue is purified over silica gel using n-hexane/ether as a solvent and then is recrystallized from n-hexane/ether. Yield: 69.9 g, corresponding to 92.8% of the theoretically obtainable amount.

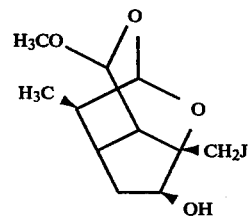

(CV)

Empirical formula: $C_{11}H_{17}O_4J$
Molecular weight: 340.166
mp: 92°–93°
$[\alpha]_D^{20}$ = −35.3° in methanol C. Preparation of 3-iodomethyl-4β-acetoxy-8-methoxy-10-methyl-2,9-dioxatricyclo[4,3,1,0³,⁷] decane (CVI) from 3-iodomethyl-4β-hydroxy-8-methoxy-10-methyl-2,9-dioxatricyclo[4,3,1,0³,⁷] decane (CV).

20 g of 3-iodomethyl-4β-hydroxy-8-methoxy-10-methyl-2,9-dioxatricyclo[4,3,1,0³,⁷] decane are dissolved in 20 ml of pyridine and 10 ml of acetic anhydride and the solution is allowed to stand at room temperature for 1 hour. Then ether is added and the reaction mixture is evaporated to dryness. This is repeated several times. After the residue has been purified over silica gel using n-hexane/ether as a solvent, 15.4 g of the compound are obtained. This corresponds to 68.5% of the theoretically obtainable amount.

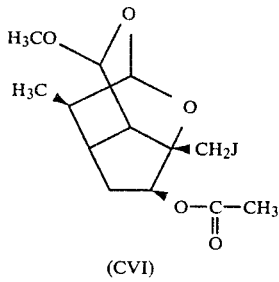

(CVI)

Empirical formula: $C_{13}H_{19}O_5J$
Molecular weight: 382.202
mp: 120°–123° C.
$[\alpha]_D^{20} = +24.8°$ in methanol

EXAMPLE 16

Preparation of 3-[1-azabicyclo(3,2,2)nonanyl]methyl-4β-hydroxy-8-methoxy-10-methyl-2,9-dioxatricyclo [4,3,1,0³,⁷] decane hydrogentartrate (CXI) from 3-iodomethyl-4β-acetoxy-8-methoxy-10-methylene-2,9-dioxatricyclo [4,3,1,0³,⁷] decane (VIII).

100 ml of dimethylformamide are added to 7.6 g of (VIII) and 10 g of sodium hydrogen carbonate. Then 7.5 g of 3-azabicyclo (3,2,2) nonane are added. The mixture is heated to 170° C. (in an oil bath) for 6 hours and then is cooled to room temperature. The mixture is evaporated and 40 ml of water and 8 ml of a 30% solution of sodium hydroxide are added to the residue. Then it is extracted 3 times with 20 ml of ether each. The ether extracts are evaporated and 5.8 g of 3-[1-azabicyclo[3,2,2)nonanyl]methyl-4β-hydroxy-8-methoxy-10-methylene-2,9-dioxatricyclo[4,3,1,0³,⁷] decane (CIX) are obtained.

5.8 g of (CIX) are dissolved in methanol. 4 g of Rainey nickel and 0.8 g of sodium hydroxide are added and the mixture is hydrogenated with hydrogen. When the hydrogen uptake has stopped, the mixture is filtered by suction over theorite which is then washed with methanol.

1.2 ml of acetic acid are added to the filtrate, the filtrate is evaporated, the residue is dissolved in ether and purified by column chromatography over silica gel (particle size: 0.2–0.5 mm). The elution is effected with n-hexane to which 1.5% of diethylamine is added. After evaporating the eluate, 4.4 g of crystalline 3-[1-azabicyclo(3,2,2)nonanyl]methyl-4β-hydroxy-8-methoxy-10-methyl-2,9-dioxatricyclo[4,3,1,0³,⁷] decane (CX) are obtained.

4 g of (CX) are dissolved in 8 ml of ethanol, then a solution of 1.94 g L(+)-tartaric acid in 13.6 ml of ethanol is added. After evaporating the solvent and drying the substance, 5.7 g of crystalline (CXI) are obtained.

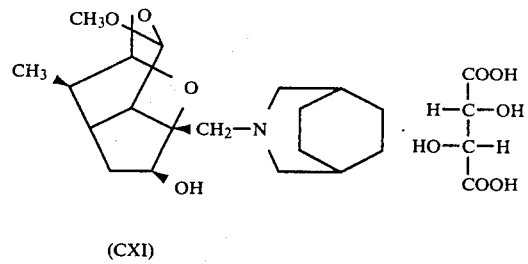

(CXI)

Empirical formula: $C_{23}H_{37}NO_{10}$
Molecular weight: 487.55
mp: 78°–81° C.
$[\alpha]_D^{20}: +7.7°$ in methanol

EXAMPLE 17

CAPSULES FOR ORAL APPLICATION

| | |
|---|---|
| 3-piperidinomethyl-4β-hydroxy-8-methoxy-10-methyl-2,9-dioxatricyclo[4,3,1,0³,⁷] decane hydrochloride | 20 g |
| lactose | 60 g |
| starch | 18,5 g |
| magnesium stearate | 1,5 g |

The components are thoroughly mixed and the mixture is filled into gelatine capsules in portions of 100 mg per capsule.

EXAMPLE 18

One capsule, which is prepared according to Example 18, is administered to an adult person at night for the treatment of sleep disorders.

EXAMPLE 19

Preparation of 4-acetoxy-8-hydroxy-3-iodomethyl-10-methylene-2,9-dioxatricyclo [4,3,1,0³,⁷] decane (VIII) from a 66% strength didrovaltrate extract.

425 g of extract were dissolved in one liter of acetic acid at 60° C., then a mixture of 130 ml of hydriodic acid (57% strength) and 1 liter of water was added to the solution, and the mixture was left to stand for 2 hours at 60° C., with occasional stirring.

WORKING UP:

After addition of 100 g of activated charcoal, suction filtration over Theorit (tradename = fire resistant asbestos wool) was effected, followed by thorough washing with 4 liters of ether. 3 liters of water were added to the filtrate, thorough shaking was effected, and the ether phase was separated off. This was then washed with alkaline, once with 2 liters of water and once with soda solution (1.5 kg of sodium carbonate in 8 liters of water). The three water phases were then extracted individually 3 times with, in each case, 2 liters of ether. The combined ether phases were dried over 1 kg of sodium sulfate, treated with 100 g of activated charcoal, suction filtered over Theorit and then concentrated in a vacuum at 30°–40° C. in a round flask, with addition of 18 ml of water; II crystallized. After rubbing with ether and filtration over a suction filter, 170 g of crude crystalline product was obtained representing 70% of theoretical yield.

Empirical Formula: $C_{12}H_{15}O_5I$

Molecular weight: 366.14
m.p.: 152°–156° C. (Kofler, uncorrected)
$[\alpha]_C^{+22°\ C.}: +142°$ (methanol)

What is claimed is:

1. A compound selected from the group of 2,9-dioxatricyclo [4,3,1,0$^{3,7}$] decanes of formula I

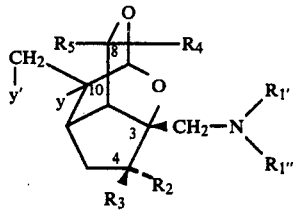

wherein $R_{1'}$ and $R_{1''}$ together with the nitrogen atom to which they are bound form a cyclic amino group selected from the group consisting of indolinyl and groups of the formula

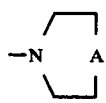

wherein A represents oxygen or a group >N-A' wherein A' represents an alkyl group containing 1 to 4 carbon atoms which is unsubstituted or substituted in ω-position by a substituent which is selected from the group consisting of hydroxy, acyloxy, carbamyloxy, pyridyl, or a phenyl or benzhydryl group, the phenyl rings of which are unsubstituted or substituted by halogen;

one of $R_2$ and $R_3$ is hydrogen and the other represents hydroxy, an acyloxy group Z—COO— wherein Z is alkyl or alkenyl, containing 1 to 4 carbon atoms, or phenyl, or a carbamyloxy group Z—NHCOO— wherein Z is alkyl or alkenyl, containing 1 to 4 carbon atoms or phenyl, or $R_2$ and $R_3$ jointly represent oxygen;

one of $R_4$ and $R_5$ is hydrogen and the other represents an alkoxy group containing 1 to 6 carbon atoms, or an aralkyloxy group containing 7 to 9 carbon atoms;

and y and y' each represent hydrogen or jointly form a bond;

and pharmaceutically acceptable acid addition salts thereof.

2. The compound as defined in claim 1 having the formula (I d)

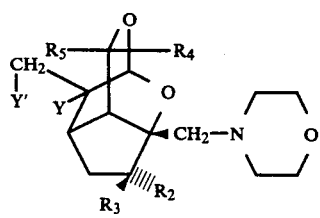

3. The compound as defined in claim 1 having the formula (I e)

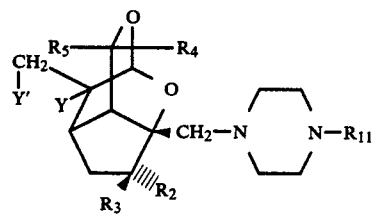

wherein $R_{11}$ represents an alkyl group containing 1 to 4 carbon atoms which is unsubstituted or is substituted in its ω-position by hydroxy, acyloxy or carbamyloxy, phenyl, pyridyl or halobenzhydryl.

4. The compound as defined in claim 1 having the formula (I f)

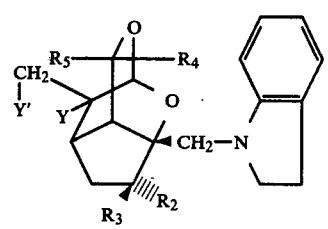

5. The compound as defined in claim 1 which is

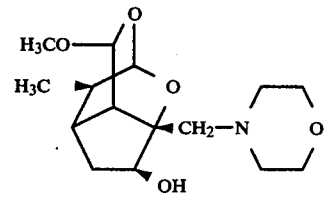

3-morpholinomethyl-4β-hydroxy-8-methoxy-10-methyl-2,9-dioxatricyclo [4,3,1,0$^{3,7}$] decane of the formula (V), and its pharmacologically acceptable acid addition salts.

6. A pharmaceutical composition comprising an inert carrier material and a sedatively or saporifically effective amount of a compound as defined in claim 1.

7. A method for sedating larger mammals comprising the step of administering to a larger mammal the pharmaceutical composition as defined in claim 6.

8. A method for increasing and improving sleep in larger mammals comprising the step of administering to a larger mammal the pharmaceutical composition as defined in claim 6.

9. A method of sedating or increasing and improving sleep in larger mammals comprising the step of administering to a larger mammal 0.075 to 1 mg/kg of a compound as defined by claim 1.

10. The method of treatment as defined by claim 9, wherein the administering step comprises administering a daily dosage of from about 5 to 50 mg of said compound.

* * * * *